US006245036B1

United States Patent
McRoberts et al.

(10) Patent No.: US 6,245,036 B1
(45) Date of Patent: Jun. 12, 2001

(54) MALE GENITALIA SUPPORT GARMENT

(75) Inventors: Samuel J. McRoberts, North Palm Beach; Lee Kvarnberg, Jupiter, both of FL (US)

(73) Assignee: Male Pouch, Inc., North Palm Beach, FL (US)

( * ) Notice: Subject to any disclaimer, the term of this patent is extended or adjusted under 35 U.S.C. 154(b) by 0 days.

(21) Appl. No.: 09/152,455

(22) Filed: Sep. 14, 1998

Related U.S. Application Data

(63) Continuation-in-part of application No. 08/699,595, filed on Aug. 19, 1996, now Pat. No. 5,807,299.

(51) Int. Cl.⁷ ..................................................... A61F 13/00
(52) U.S. Cl. ................................ 602/67; 602/70; 602/73; 2/2; 2/403
(58) Field of Search ................................... 128/845, 846; 602/67, 70, 72, 73; 2/2, 403

(56) References Cited

U.S. PATENT DOCUMENTS

| | | |
|---|---|---|
| 64,766 | 5/1867 | Heaton . |
| 77,757 | 5/1868 | Phelps . |
| 214,888 * | 4/1879 | Cooper .................................. 602/73 |
| D. 233,633 | 11/1974 | Burkard . |
| 265,672 | 10/1882 | Hart . |
| 286,657 | 10/1883 | Ware . |
| 531,232 | 12/1894 | Teuscher, Jr. . |
| 713,318 | 11/1902 | Lovis . |
| 850,298 | 4/1907 | DeMars . |
| 908,533 | 1/1909 | Zuckriegel . |
| 967,736 | 8/1910 | Delp . |
| 1,019,501 | 3/1912 | Love et al. . |
| 1,023,478 | 4/1912 | O'Reilly . |
| 1,052,765 * | 2/1913 | Strauss ................................... 602/67 |
| 1,350,863 | 8/1920 | Fowler . |
| 1,477,187 | 12/1923 | Rayne . |
| 1,483,351 | 2/1924 | Keirstead . |
| 1,638,525 | 8/1927 | Chisholm . |
| 1,742,399 | 1/1930 | Klein . |
| 2,293,998 | 8/1942 | Norwood . |
| 2,320,736 | 6/1943 | Nevins . |
| 2,427,428 | 9/1947 | Vitale . |
| 2,686,517 | 8/1954 | Boyd . |
| 2,746,456 | 5/1956 | Johnson . |
| 2,798,484 | 7/1957 | Boudreaux . |
| 2,888,014 | 5/1959 | Dougherty . |
| 3,225,761 | 12/1965 | Swensen . |
| 3,314,422 | 4/1967 | Phillips . |
| 3,518,995 | 7/1970 | Claff . |
| 3,550,590 | 12/1970 | Keilman . |
| 4,122,849 | 10/1978 | Dietz . |
| 4,141,357 | 2/1979 | Dietz . |
| 4,195,630 | 4/1980 | Connery et al. . |
| 4,505,707 | 3/1985 | Feeney . |
| 4,576,599 | 3/1986 | Lipner . |
| 4,627,846 | 12/1986 | Ternström . |
| 4,660,554 | 4/1987 | Wright . |
| 4,731,063 | 3/1988 | Newkirk . |
| 5,029,345 | 7/1991 | Angheluta et al. . |
| 5,157,793 | 10/1992 | Michels . |
| 5,275,592 | 1/1994 | Grizzaffi . |
| 5,401,266 | 3/1995 | Runeman et al. . |
| 5,524,298 * | 6/1996 | Plunkett ................................. 602/67 |
| 5,547,466 * | 8/1996 | McRoberts ............................. 602/70 |

FOREIGN PATENT DOCUMENTS 221903   5/1910   (DE) .

* cited by examiner

Primary Examiner—Michael A. Brown
(74) Attorney, Agent, or Firm—Howrey Simon Arnold & White, LLP

(57) ABSTRACT

A male genitalia support garment has a posterior testicular strap portion extending from a waist band portion of the garment. The posterior testicular strap portion is designed to be positioned behind the scrotum and the testicles to provide support to the wearer's scrotal contents. The posterior testicular strap portion is made of a generally unyielding material in the dynamic state so that a constant, non-variable amount of support is provided to the wearer.

13 Claims, 7 Drawing Sheets

MALE GENITALIA SUPPORT GARMENT

This is a continuation in part application from Ser. No. 08/699,595 filed on Aug. 19, 1996 of McRoberts et al., now U.S. Pat. No. 5,807,299.

TECHNICAL FIELD OF THE INVENTION

This invention relates to support devices for male genitalia, and more particularly, to a garment to be used as a support device for male genitalia.

BACKGROUND OF THE INVENTION

Support garments for male genitalia are well known. Typical support garments have a cup shaped support secured to the male body by either an elastic waist band or an elastic waist band in combination with leg straps.

U.S. Pat. No. 4,141,357 issued to Dietz discloses a cup supporter that utilizes a spherical shaped pouch with an elastic band having two attachment straps to fasten the cup supporter to an undergarment. The amount of length and tension of the elastic band is adjusted for the comfort of the wearer. The elastic band is located on the anterior side of the lower torso region.

Also, U.S. Pat. No. 4,122,849 issued to Dietz discloses yet another cup supporter with an elastic waist band. This cup supporter provides shape to the wearer's genitalia region by shaping the male genitalia while worn. The pouch is made from a laminate sheet of foam rubber. Elastic is sewn to the top edge of the pouch, which is attached to an elastic strap that is to be placed around the waist of the wearer. The elastic is to be adjusted for the comfort of the wearer and to adjust the amount of support given by the supporter. The cup's shape changes as the elastic band at the top edge of the cup is stretched.

Typical supporters attempt to provide a comfortable and lightweight supporter that provides continuous and steady support to the male genitalia. Nevertheless, the typical supporters have designs that are insufficient in the amount of continuous and non-variable support given to the male genitalia, and more particularly, to the support of the scrotum and the testicles to prevent excessive strain upon the cremaster muscle and the spermatic cords.

Such a support of the scrotum and testicles is desired after minor surgery, such as a vasectomy, or during and after a case of epididymitis, where support of the cremaster muscles and the spermatic cords aids in the patient's healing process and raises the patient's comfort level during these events.

Most particularly, the supporters of the past do not adequately address the need of providing a supporter that is integrated into a garment, whether the garment is used as underwear or used as active wear. Active wear may include garments used as swim wear, surfing shorts, bicycle shorts, baseball pants or other athletic clothing.

In addition, supporters of the past do not allow the passage of air for ventilation of the wearer's genital area. Without ventilation, the wearer would become hot and perspiration would occur. The wearer would become uncomfortable and would be prone to the growth of fungi and bacterial infections at the genital region. The growth of fungi and bacteria in the genital region should be avoided, especially after surgery in the genital area. A surgical incision after surgery should have an adequate amount of ventilation of fresh air to promote healing.

Most of the available supporters are designed to be made of a generally yielding material so that the supporter flexes with the movement of the wearer. For example, Dietz (U.S. Pat. No. 4,122,849) discloses the use of an elastic strap at the top edge of the pouch so that the cup's shape and cubic volume fluctuates as the wearer moves about and the elastic is stretched. Therefore, as the wearer of the supporter would move about in the his daily activities, and as the lower torso moves, the cup's shape would be constantly fluctuating in shape and cubic volume, which would result in a varying amount of support given to the wearer's scrotum and testicles. The basic design of the currently available supporters would be uncomfortable to an every day user absent surgery or illness.

Therefore, what is needed is a support garment for male genitalia that emphasizes support at the scrotum for the testicles, and more particularly, a support garment for the scrotal contents and cords.

DISCLOSURE OF THE INVENTION

It is, therefore, an object of the present invention to provide a male genitalia support garment that provides generally a constant and non-variable amount of support to the testicular muscles and cords.

It is also an object of the present invention to provide a male genitalia support garment that is integrated into clothing, such as underwear, boxer shorts, swim suits and active wear.

It is also an object of the present invention to provide a male genitalia support garment that is lightweight and comfortable to wear.

It is also an object of the present invention to provide a male genitalia support garment that provides for the ventilation of air at the genitalia region while being worn.

It is also an object of the present invention to provide a male genitalia support garment that supports the scrotum and testicles to prevent excessive strain upon the cremaster muscles and the spermatic cords, or generally, the testicular muscles and cords.

It is also an object of present invention to provide a male genitalia support garment that may be used after surgery, such as a vasectomy, herniorrhaphy, or during and after an illness, such as a case of epididymitis or hydrocele, where the supporter aids in the patient's healing process and raises the patient's comfort level during these events.

It is also an object of the present invention to provide a male genitalia support garment that provides generally a constant, non-variable amount of support to the posterior side of the scrotum and testicles, and more particularly, to the cremaster muscles and the spermatic cords.

According to the present invention, a male genitalia support garment has a posterior testicular strap portion extending from a waist band portion. The posterior testicular strap portion is designed to be positioned behind the scrotum and testicles. The posterior testicular strap portion is an extension of the waist band portion, so that the waist band portion provides support to the testicular strap portion while the supporter is worn. A receptacle for accepting the male's genitalia may be attached to the support, the receptacle extends from the posterior testicular strap portion. The receptacle accepts and houses the wearer's scrotum, testicles, and penis.

The posterior testicular strap portion establishes a line of support for the scrotum and testicles. In a first embodiment, the waist band portion and the testicular strap portion are made of a material that is generally non-elastic or that is generally unyielding while experiencing tensile stresses, such as a ⁵⁄₁₆ths wide weaved cotton material. The weave is similar to an athletic shoestring weave. The generally unyielding material provides a constant and non-variable line of support to the cremaster muscles and the spermatic cords, or generally, the testicular muscle and cords.

In the first embodiment, the posterior testicular strap and the waist band portions are secured to a garment or an inner liner of a garment, typically by sewing the portions directly to the garment or the inner liner. The garment or inner liner has a receptacle for accepting the male's genitalia. A variety of garment or inner liner sizes would be available to accommodate the variety of sizes reflected the general male population.

The receptacle in the garment or in the inner liner is preferably made from a lightweight and air-permeable fabric, such as cotton or silk. The fabric is constructed to create a receptacle for the scrotum, testicles, and penis.

In the second and third embodiments, a male genitalia support garment has a posterior testicular strap portion that extends from or is adjacent to a waist band portion of a garment. A receptacle for housing the male genitalia may be attached to the posterior testicular strap and the waist band portion. The posterior testicular strap portion is preferably made from a fabric portion adjacent to an elastic portion, with both of these two portions joined by a connector, or stitching portion. The stitching portion determines the length and the amount of support given by the posterior testicular strap in its dynamic state, or while in use. The elastic portion retracts the posterior testicular strap and the attached receptacle while in a static state, or while not in use. The dynamic state also allows the posterior testicular strap to be self adjusting at the point of being put on by the wearer.

In the preferred embodiment, the elastic portion is stretched to a preselected small percentage of the maximum stretchability of the material. Then the elastic portion is stitched to the fabric portion creating a limited amount of stored potential energy, or limited amount of maximum stretch, in the posterior testicular strap. The preselected amount of potential energy in the elastic portion is less than the amount of support needed for the male genitalia, so that the elastic portion itself does not provide the support to the male genitalia. Instead, the stitching portion provides the support given by the posterior testicular strap to the male genitalia. As in the above mentioned first embodiment, a variety of sizes would be available to accommodate different individuals.

In all three of the above embodiments, a garment is provided with a posterior testicular strap portion that establishes a line of support for the scrotum and testicles. All of the above mentioned embodiments utilize material that is generally non-elastic or generally unyielding in their dynamic states, therefore, the line of support provides generally a constant and non-variable amount of support to the testicular muscles and cords.

The foregoing and other advantages of the present invention will become more apparent from the following description and accompanying drawings.

BEST MODE FOR CARRYING OUT THE INVENTION

Figure 1:
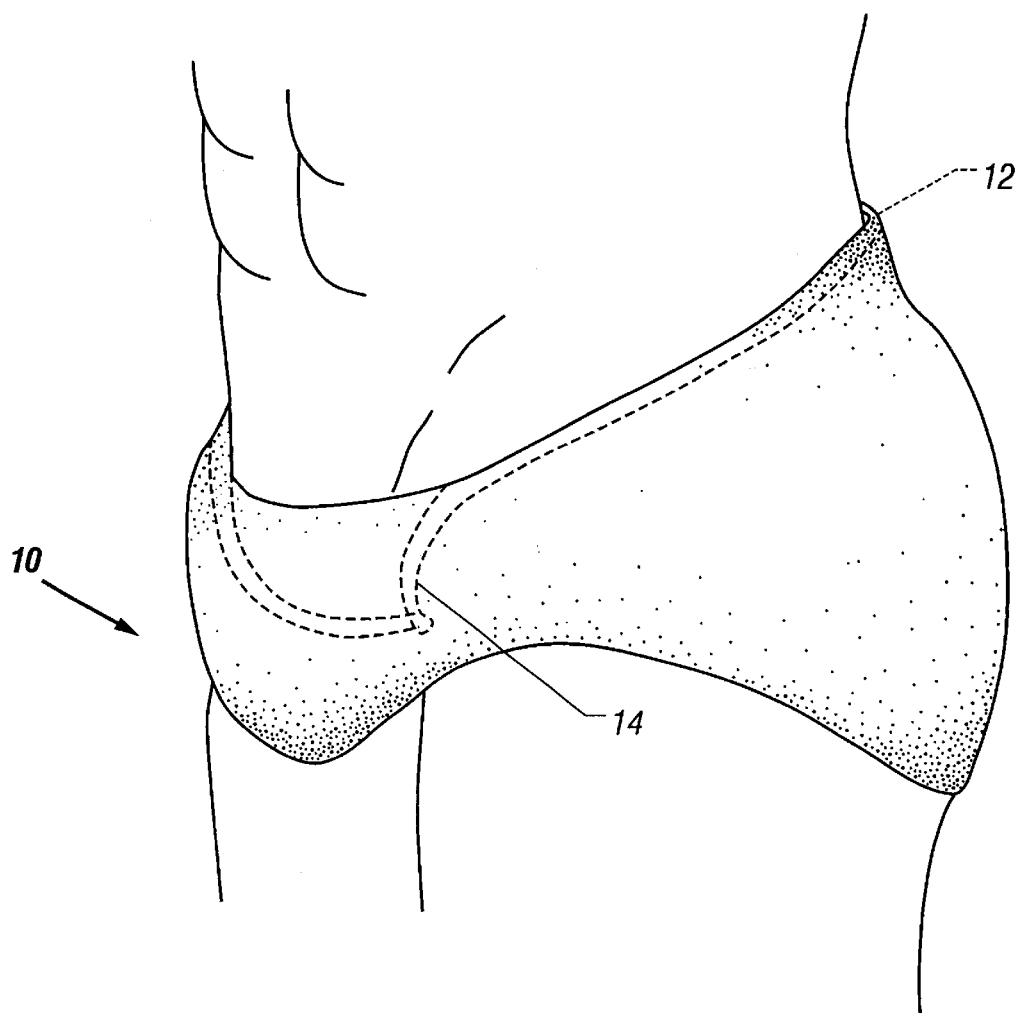
FIG. 1 is a front perspective view of a male genitalia support garment of the present invention, as worn by the wearer.

According to the present invention, and as shown in FIG. 1, a male genitalia support garment 10 is provided to give support to the wearer's scrotum and testicles.

The scrotum is a pouch of skin lying below the pubic symphysis and in front of the upper parts of the thighs. The scrotum contains the testes, or both testicles, and the lowest parts of the spermatic cords.

Below the skin of the scrotum is a layer of involuntary muscle, the dartos, which alters the appearance of the scrotum. The cremaster muscle is a thin muscle layer covering the spermatic cord through which sperm travels. The function of the cremaster muscles is to pull the testicles toward the body in response to cold temperature or stimulation to the nerves.

Beneath the dartos muscle are layers of fascia continuous with those forming the coverings of each of the two spermatic cords, which suspend the testes within the scrotum and contain each ductus deferens, the testicular blood and lymph vessels, the artery to the cremaster muscles, the artery to each ductus deferens, the genital branch of the genitofemoral nerve, and the testicular network of nerves. Therefore, each cord is made up of arteries, veins, lymphatics, nerves, and the excretory duct of the testicles. The spermatic cord is the structure by which each testicle is attached to the body. The left spermatic cord is usually longer than the right, thus the left testis usually hangs lower than the right.

The testes each have an epididymis, which is a long tightly coiled tube that ends in a single tube called the vas deferens, which empties into an ejaculatory duct in the posterior urethra, which carries sperm from the testicle to the tip of the penis. Epididymitis is an inflammation of the epididymis. Epididymitis may result from urinary infection, venereal disease, prostate surgery or trauma.

In regards to the present invention, the cremaster muscles and spermatic cords, and more generally, the muscles, cords, and ducts that attach and connect the testicles to the pelvis area and the body in general, are referred to in a general sense as testicular muscles and cords.

Figure 2:
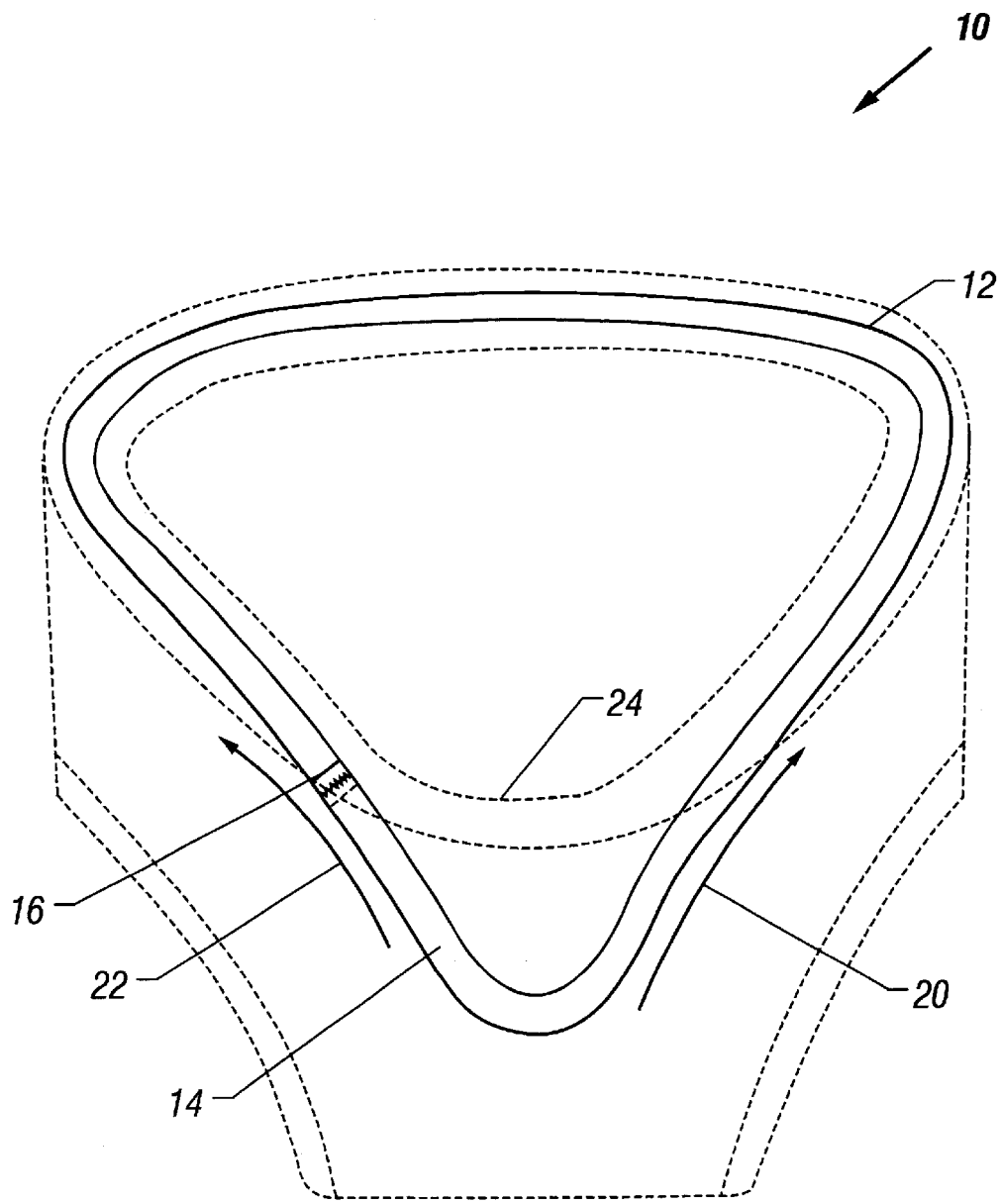
FIG. 2 is a rear perspective view of the male genitalia support garment of the present invention, with the support portion shown in solid and the garment portion shown in phantom.

As shown in FIG. 1, the male genitalia support garment 10 has a waist band portion 12 that is to placed around the waist of the male wearer. Referring now to FIG. 2, the male genitalia support garment 10 also has a posterior testicular strap portion 14 extending from the waist band portion 12. As shown in FIG. 2, the waist band portion 12 and the posterior testicular strap portion 14 may be one continuous strap that is sewn together at a juncture of the two portions 16.

In the first embodiment, the posterior testicular strap portion 14 and the waist band portion 12 are secured or sewn into a garment, a piece of clothing or an inner liner of a garment, such as a swimsuit or other active wear. In the first embodiment, the posterior testicular strap and the waist portions are sewn directly to the garment or the inner liner. The garment or inner liner has a receptacle 26 for accepting the male's genitalia. A variety of garment or inner liner sizes would be available to accommodate the variety of sizes reflected the general male population. In addition, a variety of garment or inner liner sizes could be available in each size that would provide a variety of support levels. The support level provided is dependent upon the total length of the posterior testicular strap and the waist band portions.

The receptacle 26 in the garment or in the inner liner is preferably made from a lightweight and air-permeable fabric, such as cotton or silk. The posterior testicular strap portion 14 is sewn to the garment is a manner to create the receptacle 26 for the scrotum, testicles, and penis.

When the posterior testicular strap portion 14 is placed on the posterior side of the scrotum and testicles and the waist band portion 12 is placed around the wearer, support or lift is provided along the posterior testicular strap 14, as generally shown by arrows 20 and 22.

The male genitalia support garment 10 may include a lateral strap portion 24, connecting to the posterior testicular strap 14. When placed on the wearer, the lateral strap portion 24 extends across the anterior lower torso area of the wearer. Minimal load is experienced at the lateral strap portion 24. In the first embodiment, the lateral strap portion 24 is provided by the garment or the inner liner. In the case of sewing the posterior testicular strap portion and the waist portion to an existing pair of underwear, the lateral strap portion 24 will include an elastic portion so that the garment may placed over the hips of the wearer. The remaining elastic portion of the waist band of the underwear would become nonfunctional since the waist band portion 12 would be sewn to the elastic waist band of the underwear. In this embodiment, the lateral strap portion is about 20 percent of the total circumference of the waist band of the garment. The location of the lateral strap portion is in a minimal load bearing location since most of the support load is carried away from the lateral strap portion 24 in the direction of arrows 20 and 22.

In the first embodiment, the amount of stored energy, or potential energy, in the lateral strap portion 24 would be less than the amount of support provided by the posterior testicular strap portion 14, shown by arrows 20 and 22.

Figure 4:
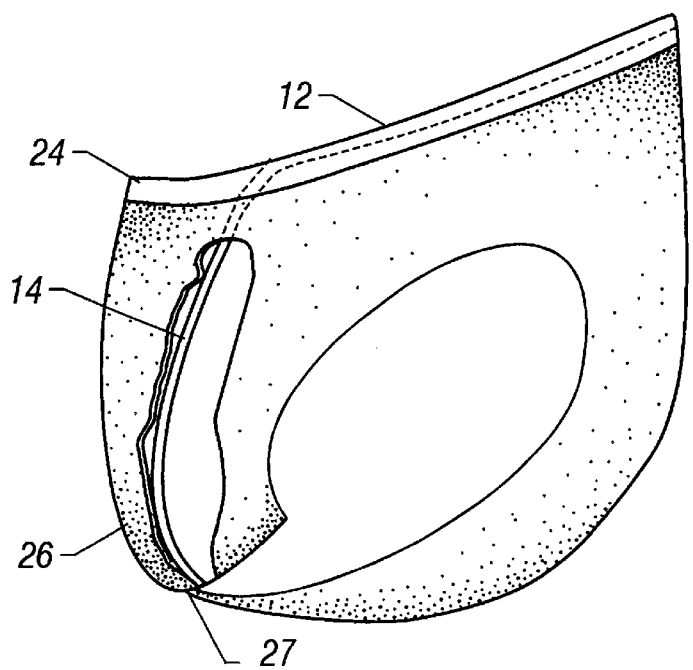
FIG. 4 is a partial cross sectional view of the male genitalia support garment of the present invention.

The functional purpose for the lateral strap portion 24 is so that a receptacle 26 may be attached to the posterior testicular strap 14 and to the lateral strap portion 24. The receptacle 26 accepts and houses the wearer's scrotum, testicles, and penis. The receptacle 26 provides only minor and secondary support to the testicles; the primary lifting and support of the testicles is provided by the posterior testicular strap 14. As shown in FIG. 4, the receptacle 26 is sewn to the posterior testicular strap portion 14 at juncture 27.

Figure 3:
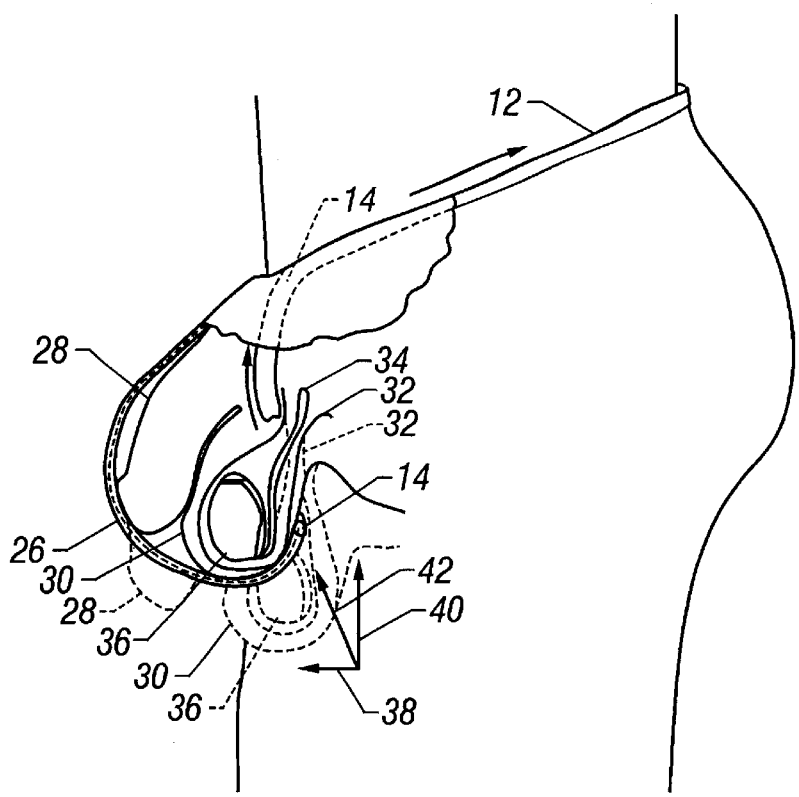
FIG. 3 is cross sectional view of the male genitalia support garment of the present invention showing the area of support given to the male genitalia of the wearer.

Referring now to FIG. 3, the male genitalia support 10 is shown in a cross sectional view as worn by the wearer. The wearer's penis 28 is shown housed in the receptacle 26, as is the wearer's scrotum 30 and testis 36. The cremaster muscle 32 is shown surrounding the spermatic cord 34; the cremaster muscle 32 supports the testes 36. The posterior testicular strap portion 14 is shown on the posterior side of the scrotum 30 and testis 36.

As the posterior testicular strap portion 14 is supported by the waist band portion 12, a horizontal force vector 38 and a larger vertical force vector 40 combine to give the resultant force vector 42. The resultant force vector, or line of support 42 lifts and supports the testicular muscles and cords of the wearer, relieving the testicular muscles and cords from tensile forces and strain.

The waist band portion 12 and posterior testicular strap 14 in the first embodiment are made of a generally non-elastic and generally unyielding material, or yields only a relatively small amount when placed under tensile stress, in the dynamic state, or while being worn, so that the amount of support given to the testicular muscles and cords is a constant and non-variable lifting support. As the wearer walks, sits, or stands, the support given to the testicular muscles and cords is non-variable. This non-variable amount of support, together with the comfort given to the wearer, combine to be key advantages of the male genitalia support 10 over the prior support garments.

The male genitalia support 10 is particularly useful after surgery to the male genitalia area, such as a vasectomy or herniorrhaphy, or after an illness such as epididymitis or hydrocele, or after an injury to the male genitalia area. Support of the testicular muscles and cords aids in the patient's healing process and raises the patient's comfort level during these events.

The use of the male genitalia support 10, however, does not need to be limited to post-surgery, injury, or illness. The male genitalia support 10 provides an alternative undergarment or support garment for the male that provides support while having an aesthetic appearance. Therefore, the support 10 may be worn as an everyday article of clothing.

To reduce the opportunity for bacteria to grow it the male genitalia area, particularly after surgery in that area, the receptacle 26 is made from an air-permeable material, such as cotton, silk or a perforated material that allows the passage of air for the ventilation of the wearer's genitalia area. Ventilation of the area will help to reduce the temperature and perspiration. The use of the air-permeable material will increase the wearer's comfort level and reduce the possibility of the growth of fungi (most particularly, tinea cruris, or jock itch). The air-permeable material will help to ventilate the surgical incision after surgery and the ventilation of fresh air will promote healing of the incision.

Figure 5:
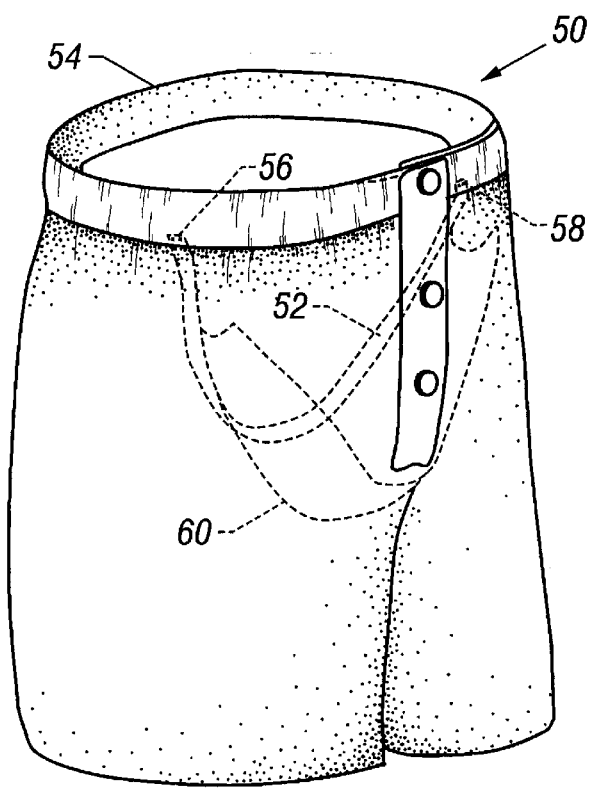
FIG. 5 is perspective view of an alternative embodiment of the present invention, wherein the male genitalia support garment is incorporated into a pair of shorts with a front opening.
Figure 6:
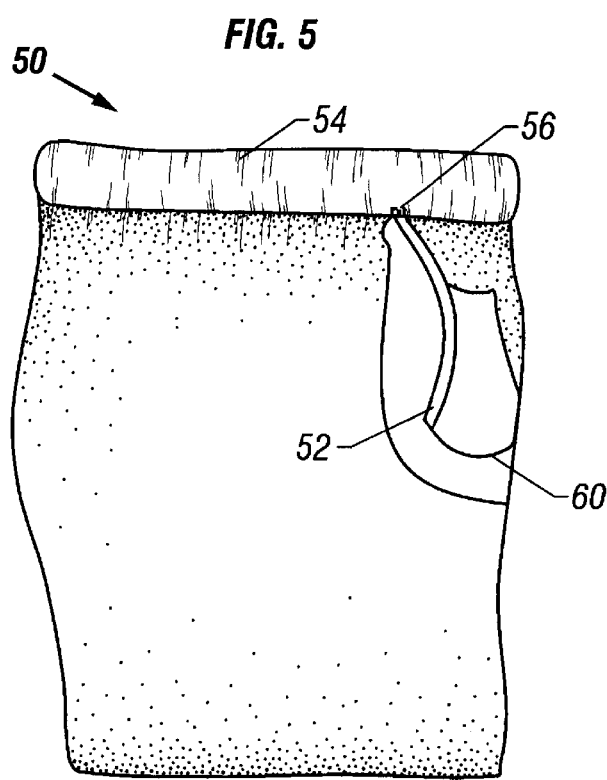
FIG. 6 is a partial cross sectional view of the perspective view of the alternative embodiment shown in FIG. 5.

Now referring to FIGS. 5 and 6, a second embodiment of the male genitalia support garment 50 is shown, which is similar to the above first embodiment shown in FIG. 1, except that the support garment 50 is integrated with a pair of shorts with a front opening, such as a pair of boxer shorts, a swimsuit, surf pants or other active wear. Nevertheless, any garment with a waist portion and a genital covering portion would suffice.

The supporter 50 has a posterior testicular strap 52 connected to a waist band 54 at a first juncture 56 and a second and opposite juncture 58. The junctures 56 and 58 are in the approximate ares of the intersections of the right and left thigh crease lines with the waist band 54. A receptacle 60 is sewn to the garment and to the posterior testicular strap 52. The waist band 54 may be of an elastic type or the draw string type. If an elastic waist band 54 is utilized, the elastic in the waist band 54 would have a potential energy, or stored energy, greater than the amount of support required of the posterior testicular strap 52 in the dynamic state, or while worn. The relationship of the waist band and the posterior testicular strap will be discussed in more detail below. Only a minimal amount is support is needed for the typical male to lift the scrotal contents, if the support is applied in the proper location, such as the location of the posterior testicular strap. The shorts shown in the second embodiment has an opening to facilitate bodily functions.

Figure 7:
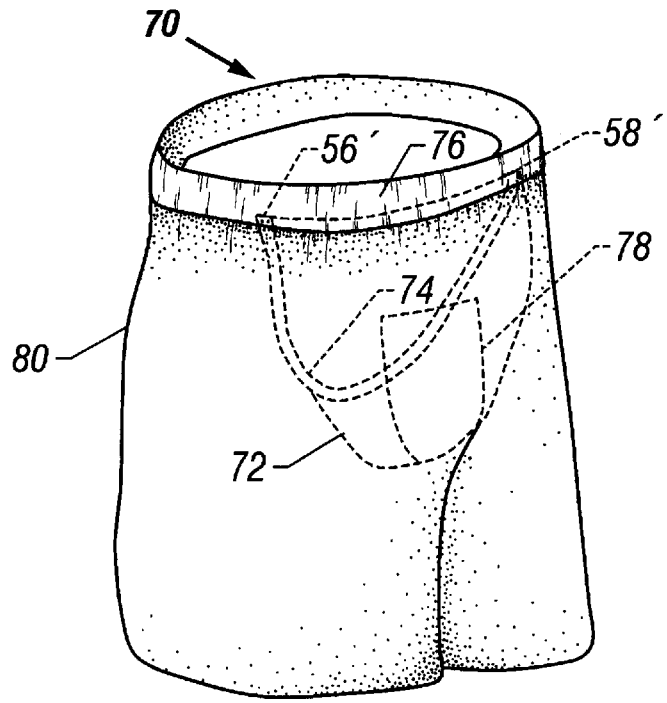
FIG. 7 is yet another separate embodiment of the present invention, wherein the male genitalia support garment is incorporated into a pair of shorts without a front opening.
Figure 8:
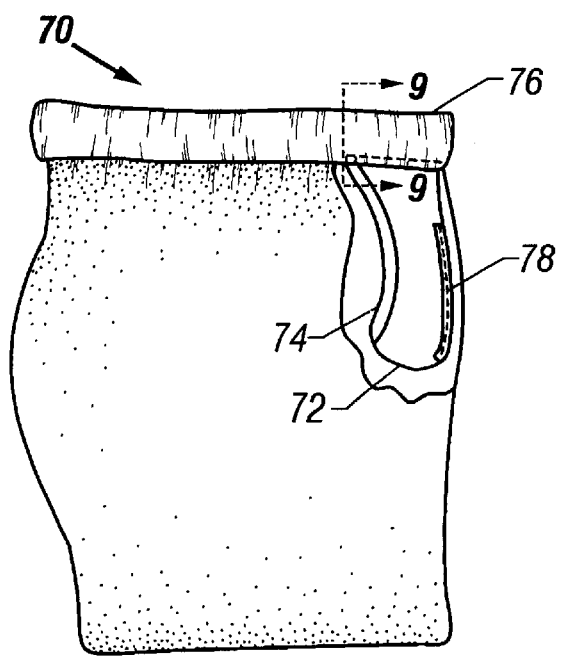
FIG. 8 is a partial cross sectional view of the perspective view of the alternative embodiment shown in FIG. 7.

Now referring to FIGS. 7 and 8, a third embodiment of a male genitalia support garment 70 is shown. This third embodiment is similar to the second embodiment shown in FIGS. 5 and 6, except as explained below. The pair of shorts shown in the third embodiment do not have a frontal opening, which is typical of bicycle shorts and other active wear shorts. Another difference is that a receptacle 72 extends from a posterior testicular strap 74 to a garment waist band 76. The receptacle has a front pouch 78 that may be used to house an athletic cup, typically used in contact sports to protect the genitalia from impact forces.

Without limiting the scope of the claims, FIGS. 9 through 12, refer to both the second and the third embodiments shown in FIGS. 5 and 7; however, the description here is directed to the third embodiment shown in FIG. 7.

Figure 9:
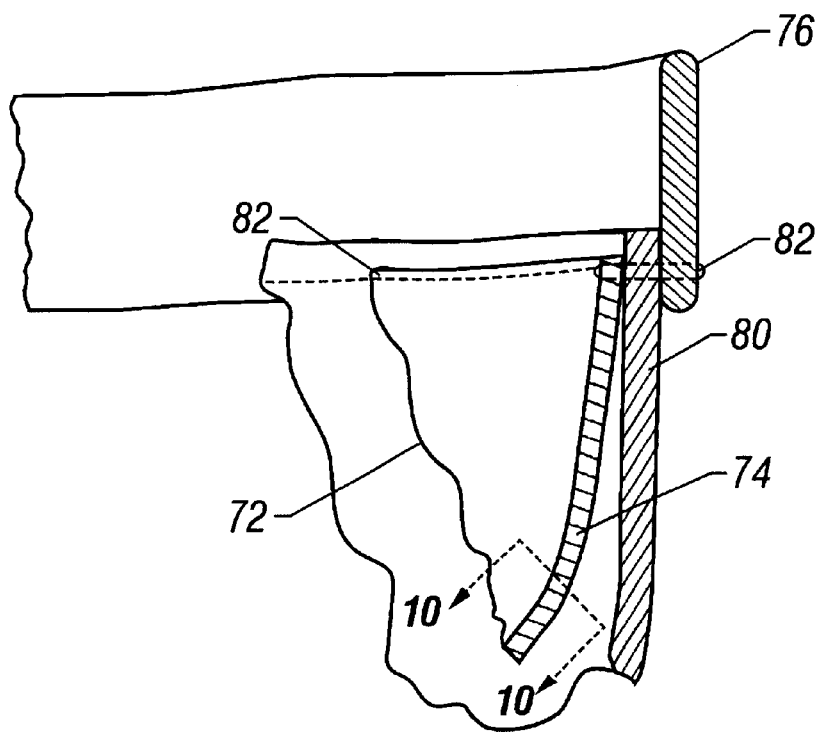
FIG. 9 is a partial cross sectional view taken from view 9—9 in FIG. 8.

Referring to FIG. 9, the garment waist band 76, fabric 80 of the garment, the posterior testicular strap 74 and the receptacle 72 are shown sewn together with stitching 82 at the juncture 56'. For the third embodiment, the stitching 82 extends from juncture 56' to 58' to secure the receptacle 72 to the garment waist band 76. It is to be understood that the support may also be sewn to the an inner liner of a garment 70.

Figure 10:
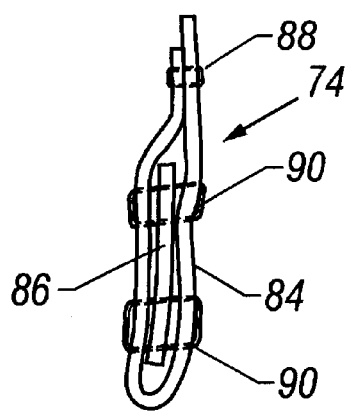
FIG. 10 is a cross sectional view taken from view 10—10 in FIG. 9.

FIG. 10 shows that the posterior testicular strap portion 74 is preferably made from a fabric portion 84 adjacent to and encircling an elastic portion 86, with both of these two portions joined by a connector, or stitching portion 90 at two locations. The fabric portion 84 is stitched together with stitching 88. The method of assembling the posterior testicular strap portion 74, and most particularly, the stitching portion 90 determines the length and the amount of support given by the posterior testicular strap portion 74 in its dynamic state, or while in use. The elastic portion 86 retracts the posterior testicular strap portion 74 and the attached receptacle 72 while in a static state, or while not in use. The method of stitching, described below, also allows the posterior testicular strap portion 74 to be self adjusting when the garment is initially put on by the wearer, or at the point of going from a static state to a dynamic state.

Figure 11:
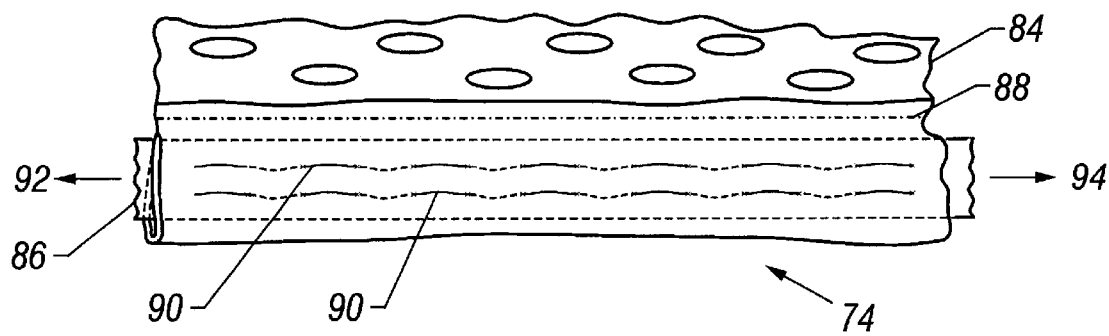
FIG. 11 is a cross sectional plan view of a posterior testicular strap construction used in the second and third embodiments, wherein the posterior testicular strap is in a dynamic state.
Figure 12:
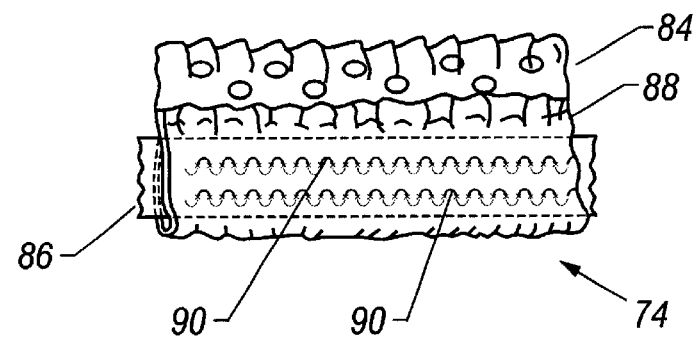
FIG. 12 is a cross sectional view of the posterior testicular strap construction used in the second and third embodiments, wherein the posterior testicular strap is in a static state.

As shown in FIGS. 11 and 12, the elastic portion 86 is stretched in the direction of arrows 92 and 94 to a preselected small percentage of the maximum stretchability of the material. Then the elastic portion 86 is sewn with stitching 90 to the fabric portion 84 creating a limited amount of stored potential energy, or limited amount of maximum stretch, in the posterior testicular strap 74. The preselected amount of potential energy in the elastic portion 86 is less than the amount of support needed for the male genitalia, so that the elastic portion 86 itself does not provide the support to the male genitalia. Instead, the stitching portion 90 provides the support given by the posterior testicular strap 74 to the male genitalia when the strap 74 is loaded or in the dynamic state. As in the above mentioned first embodiment, a variety of sizes would be available to accommodate different individuals.

Successful prototypes have been made using QUICK-STRETCH™ 3550 as the elastic material. It is available from Bemis Co. of Shirley, Mass. This material has a 300% modulus; the maximum force exerted in pulling a ¼ inch wide piece of film to 300% of its original length at a pulling rate of 30 inches/minute.

The prototype had a 14 inch piece of elastic material in the static state, which stretched to 65 inches in an unencumbered dynamic stretch test, exhibiting a minimum of a 464% stretch capability. The differential of the posterior testicular strap 74 from the static state to the dynamic state when the strap 74 was limited by the stitching portion 90, the stretch was limited to less than 6%. As worn, the 14 inch strap 74 stretched to 17 inches, representing a utilization of 5.88% of the elastic material. This minimal amount stretch utilized provides the aesthetic issue of retracting the strap 74 from the path of the feet while the garment is put on the wearer.

In all three of the above embodiments, a garment is provided with a posterior testicular strap portion that establishes a line of support for the scrotum and testicles. All of the above mentioned embodiments utilize material that is generally non-elastic or generally unyielding in their dynamic states, therefore, the line of support provides generally a constant and non-variable amount of support to the testicular muscles and cords.

Although this invention has been shown and described with respect to a detailed embodiment, those skilled in the art will understand that various changes in form and detail may be made without departing from the spirit and scope of the claimed invention. For example, separate embodiments could be provided that would include a receptacle with overlapping flaps to facilitate bodily functions or a receptacle with left and right compartments to accommodate larger left or right testicles, depending on the wearer's anatomical requirements.

Although this invention has been shown and described with respect to a detailed embodiment, those skilled in the art will understand that various changes in form and detail may be made without departing from the spirit and scope of the claimed invention.

We claim:

1. A male genitalia support garment, comprising:
   a posterior testicular strap portion adapted to be positioned on a posterior side of the wearer's scrotum and testicles when worn;
   a waist band portion that is adapted to be positioned around at least a portion of the waist of the wearer, said posterior testicular strap portion extending from said waist band portion;
   said posterior testicular strap portion having a first configuration in a static state when the male genitalia support garment is not being worn, and a second configuration in a dynamic state when the male genitalia support garment is being worn;
   said posterior testicular strap portion being made from a generally non-elastic material in the dynamic state so that said posterior testicular strap portion relieves stress from and provides support to the wearer's testicular muscles and cords.

2. The male genitalia support garment of claim 1, wherein said posterior testicular strap portion and said waist band portion are sewn into a piece of clothing.

3. The male genitalia support garment of claim 2, wherein said piece of clothing has a waist band with an elastic portion.

4. The male genitalia support garment of claim 2, wherein said piece of clothing has an elastic waist band.

5. The male genitalia support garment of claim 4, wherein said elastic waist band further comprises a potential energy that is greater than the amount of support required of said posterior testicular strap in the dynamic state.

6. The male genitalia support garment of claim 2, wherein said piece of clothing further comprises a receptacle attached to said posterior testicular strap portion, said receptacle accepting and housing the wearer's scrotum, testicles, and penis.

7. The male genitalia support garment of claim 6, wherein said receptacle is made of an air-permeable material so that ventilation is allowed through said receptacle.

8. The male genitalia support garment of claim 2, further comprising:
   a lateral strap portion extending laterally from said waist band portion and adapted to be positioned across the wearer's lower torso area.

9. The male genitalia support garment of claim 8, wherein said receptacle is attached to said posterior testicular strap portion and to said lateral strap portion.

10. The male genitalia support garment of claim 9, further comprising:
    said receptacle having a left compartment and a right compartment, one of said compartments being larger than other said compartment to accommodate for anatomical differences in testicular size, length, and shape.

11. The male genitalia support garment of claim 2, wherein said piece of clothing is available in a variety of sizes to accommodate different individual sizes or to provide different amounts of support.

12. The male genitalia support garment of claim 2, wherein said garment further comprises two flaps adapted to be pulled apart by the wearer so that said garment has an opening for the wearer's penis to facilitate bodily functions.

13. The male genitalia support garment of claim 2, wherein said posterior testicular strap portion further comprises:
    an elastic portion and a stitching portion, wherein the stitching portion determines the length and the amount of support given by the posterior testicular strap in the dynamic state.

* * * * *